United States Patent
Ray et al.

(10) Patent No.: US 6,494,862 B1
(45) Date of Patent: *Dec. 17, 2002

(54) SUBSTANCE DELIVERY APPARATUS AND A METHOD OF DELIVERING A THERAPEUTIC SUBSTANCE TO AN ANATOMICAL PASSAGEWAY

(75) Inventors: Pinaki Ray, Fremont, CA (US); Vinayak D. Bhat, Sunnyvale, CA (US); Daryush Mirzaee, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/475,727

(22) Filed: Dec. 30, 1999

Related U.S. Application Data (63) Continuation of application No. 09/352,628, filed on Jul. 13, 1999, now Pat. No. 6,283,947.

(51) Int. Cl.$^7$ .............................................. A61M 29/00
(52) U.S. Cl. ............................ 604/96.01; 604/103.01; 604/264
(58) Field of Search ................. 604/93.01, 95.03, 604/95.04, 96.01, 103.01, 103.03, 117, 181, 187, 188, 207, 211, 223, 240, 242, 264, 272, 523, 20–22; 606/7, 32, 41; 607/115, 120, 122; 600/439, 462, 466, 467

(56) References Cited

U.S. PATENT DOCUMENTS

| | | | |
|---|---|---|---|
| 3,930,761 A | 1/1976 | Barraclough | 417/476 |
| 4,465,072 A | 8/1984 | Taheri | 128/348.1 |
| 4,578,061 A | 3/1986 | Lemelson | 604/164 |
| 4,655,746 A | 4/1987 | Daniels et al. | 604/53 |
| 4,790,839 A | 12/1988 | Ahr | 604/367 |
| 4,878,904 A | 11/1989 | Callaway | 604/273 |
| 5,049,138 A | 9/1991 | Chevalier et al. | 604/265 |
| 5,112,305 A | 5/1992 | Barath et al. | 604/96 |
| 5,261,889 A | 11/1993 | Laine et al. | 604/164 |
| 5,279,565 A | 1/1994 | Klein et al. | 604/105 |
| 5,286,254 A | 2/1994 | Shapland et al. | 604/21 |
| 5,342,295 A | 8/1994 | Imran | 604/43 |
| 5,354,279 A | 10/1994 | Hofling | 604/164 |
| 5,378,230 A | 1/1995 | Mahurkar | 604/43 |
| 5,380,307 A | 1/1995 | Chee et al. | 604/264 |
| 5,415,637 A | 5/1995 | Khosravi | 604/105 |
| 5,419,777 A | 5/1995 | Hofling | 604/264 |
| 5,460,618 A | 10/1995 | Harreld | 604/264 |
| 5,462,523 A | 10/1995 | Samson et al. | 604/30 |

(List continued on next page.)

OTHER PUBLICATIONS

Kwon, et al.; Adventitial Vasa Vasorum in Balloon–injured Coronary Arteries Visualization and Quantitation by a Microscopic Three–dimensional Computed Tomography Technique; American College of Cardiology; JACC, vol. 32, No. 7; pp. 2072–2079; Dec. 1998.

(List continued on next page.)

*Primary Examiner*—Michael J. Hayes
(74) *Attorney, Agent, or Firm*—Cameron Kerrigan; Squire, Sanders & Dempsey, L.L.P.

(57) ABSTRACT

A catheter assembly is provided having a balloon disposed at the distal end thereof. The balloon is capable of being inflated to selectively dilate from a collapsed configuration to an expanded configuration. A syringe assembly is in fluid communication with a delivery lumen of the catheter assembly for allowing a therapeutic substance to be injected into a tissue of a passageway. The syringe assembly includes a portion capable of pivoting from a first position towards a second position when the balloon is being inflated from the collapsed configuration to the expanded configuration. The portion of the syringe assembly is also capable of pivoting from the second position back towards the first position when the balloon is being deflated.

9 Claims, 5 Drawing Sheets

U.S. PATENT DOCUMENTS

| | | | |
|---|---|---|---|
| 5,464,395 A | 11/1995 | Faxon et al. | 604/96 |
| 5,465,072 A | 11/1995 | Atarodi | 330/254 |
| 5,523,092 A | 6/1996 | Hanson et al. | 424/423 |
| 5,531,679 A | 7/1996 | Schulman et al. | 604/65 |
| 5,537,713 A | 7/1996 | Docteur | 16/2 |
| 5,538,504 A | 7/1996 | Linden et al. | 604/53 |
| 5,547,472 A | 8/1996 | Onishi et al. | 604/93 |
| 5,554,119 A | 9/1996 | Harrison et al. | 604/96 |
| 5,558,642 A | 9/1996 | Schweich, Jr. et al. | 604/96 |
| 5,562,630 A | 10/1996 | Nichols | 604/164 |
| 5,569,197 A | 10/1996 | Helmus et al. | 604/96 |
| 5,569,198 A | 10/1996 | Racchini | 604/96 |
| 5,626,562 A | 5/1997 | Castro | 604/53 |
| 5,628,730 A | 5/1997 | Shapland et al. | 604/21 |
| 5,643,228 A | 7/1997 | Schucart et al. | 604/264 |
| 5,681,281 A | 10/1997 | Vigil et al. | 604/96 |
| 5,693,029 A | 12/1997 | Leonhardt | 604/264 |
| 5,702,372 A | 12/1997 | Nelson | 604/264 |
| 5,709,874 A | 1/1998 | Hanson et al. | 424/423 |
| 5,713,863 A | 2/1998 | Vigil et al. | 604/104 |
| 5,746,716 A | 5/1998 | Vigil et al. | 604/97 |
| 5,749,845 A | 5/1998 | Hildebrand et al. | 604/21 |
| 5,766,152 A | 6/1998 | Morley et al. | 604/96 |
| 5,795,318 A | 8/1998 | Wang et al. | 604/8 |
| 5,797,878 A | 8/1998 | Bleam | 604/196 |
| 5,820,586 A | 10/1998 | Booth et al. | 604/53 |
| 5,833,658 A | 11/1998 | Levy et al. | 604/96 |
| 5,836,940 A | 11/1998 | Gregory | 606/15 |
| 5,865,794 A | 2/1999 | Castro | 604/53 |
| 5,866,561 A | 2/1999 | Ungs | 514/182 |
| 5,868,706 A | 2/1999 | Cox | 604/96 |
| 5,873,852 A | 2/1999 | Vigil et al. | 604/52 |
| 5,882,335 A | 3/1999 | Leone et al. | 604/96 |
| 5,902,266 A | 5/1999 | Leone et al. | 604/53 |
| 5,906,599 A | 5/1999 | Kaldany | 604/264 |
| 5,916,195 A | 6/1999 | Eshel et al | 604/96 |
| 5,941,868 A | 8/1999 | Kaplan et al. | 604/500 |
| 5,947,890 A | 9/1999 | Spencer et al. | 600/3 |
| 5,968,068 A | 10/1999 | Dehdashtian et al. | 606/192 |
| 5,971,968 A | 10/1999 | Tu et al. | 604/264 |
| 6,149,598 A * | 11/2000 | Tanaka | 600/462 |
| 6,283,947 B1 | 9/2001 | Mirzaee | 604/264 |

OTHER PUBLICATIONS

Scott, et al.; The Role of Adventitial Vasculature In Restenosis: A New View of and Old Problem; American College of Cardiology; JACC, vol. 32, No. 7; p. 2080; Dec. 1998.

\* cited by examiner

SUBSTANCE DELIVERY APPARATUS AND A METHOD OF DELIVERING A THERAPEUTIC SUBSTANCE TO AN ANATOMICAL PASSAGEWAY

CROSS-REFERENCE

This is a continuation-in-part of U.S. patent application Ser. No. 09/352,628 filed on Jul. 13, 1999, now U.S. Pat. No. 6,283,947.

BACKGROUND OF THE INVENTION

1. Field of the Invention

The present invention pertains generally to a medical device useful for delivering a substance to a biological passageway. More specifically, the present invention pertains to a catheter device having a syringe assembly useful for delivering a therapeutic substance to a passageway, such as a blood vessel.

2. Description of the Related Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

Restenosis of the artery commonly develops over several months after the procedure, which may require another angioplasty procedure or a surgical by-pass operation. Restenosis is thought to involve the body's natural healing process. Angioplasty or other vascular procedures injure the vessel walls, removing the vascular endothelium, disturbing the tunica intima, and causing the death of medial smooth muscle cells. Excessive neoinitimal tissue formation, characterized by smooth muscle cell migration and proliferation to the intima, follows the injury. Proliferation and migration of smooth muscle cells (SMC) from the media layer to the intima cause an excessive production of extra cellular matrices (ECM), which is believed to be one of the leading contributors to the development of restenosis. The extensive thickening of the tissues narrows the lumen of the blood vessel, constricting or blocking blood flow through the vessel.

To reduce the chance of the development of restenosis, therapeutic substances are administered to the treatment site. For example, anticoagulant and antiplatelet agents are commonly used to inhibit the development of restenosis. In order to provide an efficacious concentration to the target site, systemic administration of such medication often produces adverse or toxic side effects for the patient. Local delivery is a preferred method of treatment in that smaller total levels of medication are administered in comparison to systemic dosages, but are concentrated at a specific site. Local delivery, thus, produces fewer side effects and achieves more effective results.

One commonly applied technique for the local delivery of a therapeutic substance is through the use of a medicated, implantable prosthesis, one example of which includes a stent. A stent coated with a polymeric carrier, which is impregnated with a therapeutic substance, can be deployed at a selected site of treatment. The polymeric carrier allows for a sustained delivery of the therapeutic substance. A disadvantage associated with the use of medicated stents is that the quantity of the substance that can be impregnated in the polymeric carrier is limited. In order to increase the capacity of the polymeric carrier, the amount of polymeric material employed, and in effect the thickness of the coating, must be increased to accommodate the quantity of the substance used. An increase in the profile of the coating significantly limits the applications for which the stents can be used.

Another disadvantage associated with the use of medicated stents is that the polymeric carrier is only capable of applying the therapeutic substance to the inner surface of the tunica intima layer of the vessel. The polymeric carrier is incapable of significantly introducing a therapeutic substance to the tunica adventitia or the tunica media layers of the vessel. Accordingly, it is desirable to provide a substance delivery apparatus which is capable of applying any desired amount of therapeutic substances to the tunica adventitia and media layers to inhibit migration of SMC and the development of ECM.

Another commonly applied technique for the local delivery of a therapeutic substance is through the use of porous balloons attached to a distal end of a catheter assembly. The expansion of the balloon, which in effect results in the dilation of the occluded region, is accomplished by injecting a therapeutic substance into the balloon. The use of a therapeutic substance as an expansion fluid additionally functions as a medicament for the diseased region, as the therapeutic substance is discharged from the porous balloon during and subsequent to the expansion therapy. A shortcoming associated with this procedure is that the therapeutic substance is contiguously carried off in the patient's blood stream as it is being discharged from the balloon, which results in an ineffective treatment of the target site and adverse exposure of the substance to healthy tissues. Accordingly, it is desirable to provide a substance delivery apparatus that is capable of applying a therapeutic substance to the diseased region without significant loss of the substance caused by the downstream flow of blood.

SUMMARY OF THE INVENTION

A catheter assembly is provided having a balloon disposed at the distal end thereof. The balloon is capable of being inflated to selectively dilate from a collapsed configuration to an expanded configuration. The balloon is also capable of being deflated after inflation to return to the collapsed configuration or a deflated profile. A syringe assembly is in fluid communication with a delivery lumen of the catheter assembly for allowing a therapeutic substance to be injected into a tissue of a lumen. The syringe assembly includes a portion capable of pivoting from a first position towards a second position when the balloon is being inflated from the collapsed configuration to the expanded configuration. The portion of the syringe assembly is capable of pivoting from the second position back towards the first position when the balloon is being deflated.

In accordance with one embodiment, the balloon is made from a porous membrane. A therapeutic substance can be used as an inflation fluid for the porous balloon. The pores allow the therapeutic substances to be discharged out from the balloon for the local treatment of the tissues. The therapeutic substance supplied into and discharged out from the balloon can be the same as or different from the therapeutic substance administered by the syringe assembly.

In another embodiment, the delivery apparatus can include any suitable number of pivotally activated syringe assemblies. Each of the syringe assemblies can communicate with a common delivery lumen of the catheter assembly so that each of the syringe assemblies is capable of injecting the same therapeutic substance or the same combination of therapeutic substances. Alternatively, each of the syringe assemblies can be linked to an independently operated delivery lumen, allowing each of the syringe assemblies to be capable of delivering a different substance or a different combination of substances.

A method is provided for administering a therapeutic substance using the embodiments of the above described catheter assembly. The catheter assembly is inserted in a biological passageway of a subject and the syringe assembly is positioned at a desired area of treatment. The syringe assembly is pivotally rotated to cause a needle of the syringe assembly to penetrate into a wall of the desired area of treatment. A therapeutic substance is supplied through the delivery lumen of the catheter assembly to administer the therapeutic substance to the desired area of treatment.

DETAILED DESCRIPTION OF THE EMBODIMENTS

Apparatus

Figure 1:
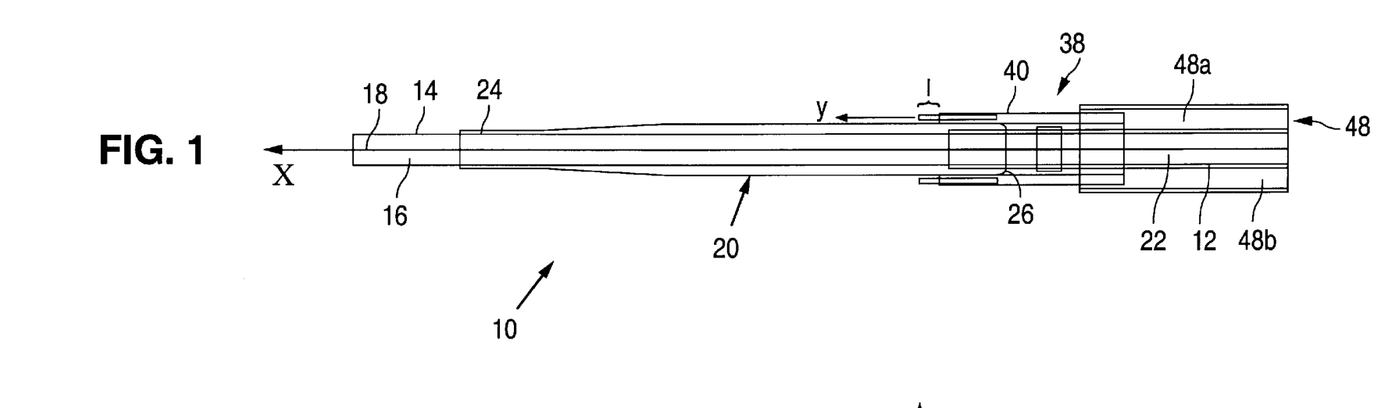
FIG. 1 is a partial cross-sectional view of one embodiment of a substance delivery apparatus of the present invention in the form of a catheter assembly having a balloon in a collapsed configuration and a syringe assembly is a rested position.
Figure 2:
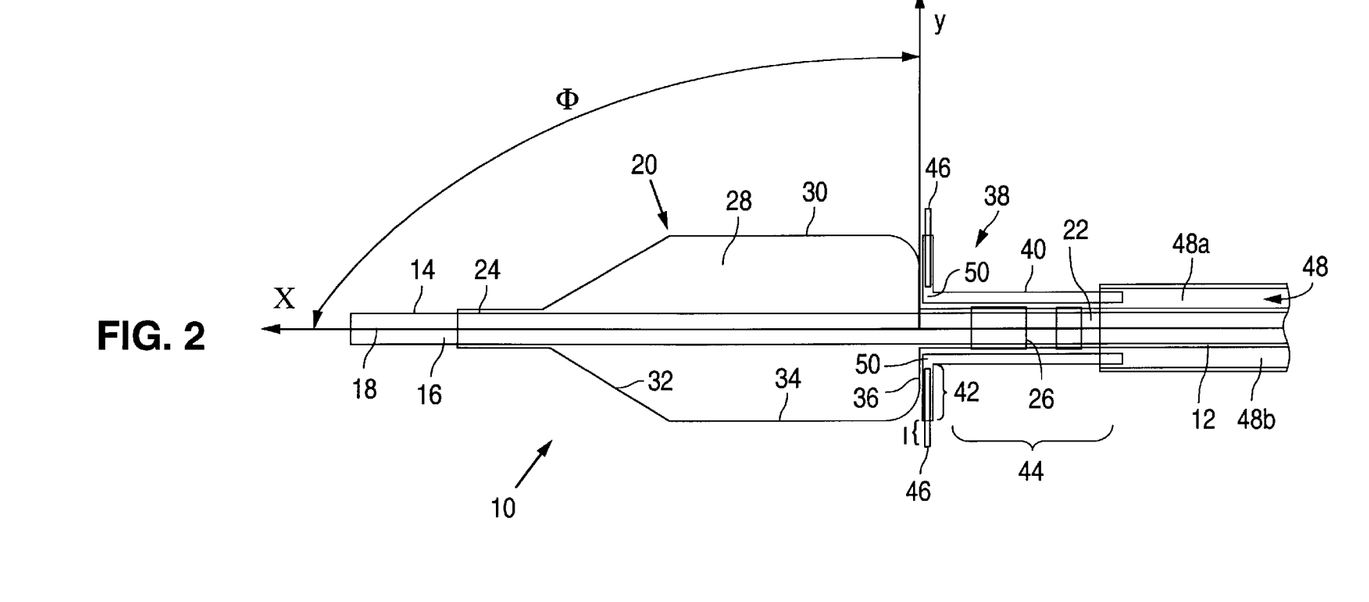
FIG. 2 is a partial cross-sectional view of the delivery apparatus of FIG. 1, illustrating the balloon in an expanded configuration and the syringe assembly pivotally rotated to a delivery position.

Referring now to the drawings, wherein similar parts are identified by like reference numerals, FIGS. 1 and 2 illustrate a substance delivery apparatus in accordance with one embodiment of the invention. In general, the substance delivery apparatus provides a system for delivering a substance, such as a therapeutic substance or a combination of therapeutic substances, to or through a desired area of a passageway in order to treat a localized area of the passageway or to treat a localized area of tissue located adjacent to the passageway. The substance delivery apparatus includes a catheter assembly 10, which is intended to broadly include any medical device designed for insertion into a body passageway to permit injection and/or withdrawal of fluids, to maintain the patency of the passageway, or for any other purpose. It is contemplated that the substance delivery apparatus has applicability for use with any biological passageway, including blood vessels, urinary tract, intestinal tract, kidney ducts, wind pipes, and the like.

Catheter assembly 10 is defined by an elongated catheter tube 12 having a proximal end (not illustrated) and a distal end 14. Catheter assembly 10 can include a guidewire lumen 16 for allowing catheter assembly 10 to be fed and maneuvered over a guidewire 18. A balloon 20 is incorporated at distal end 14 of catheter assembly 10 and is in fluid communication with an inflation lumen 22 of catheter assembly 10.

Figure 3:
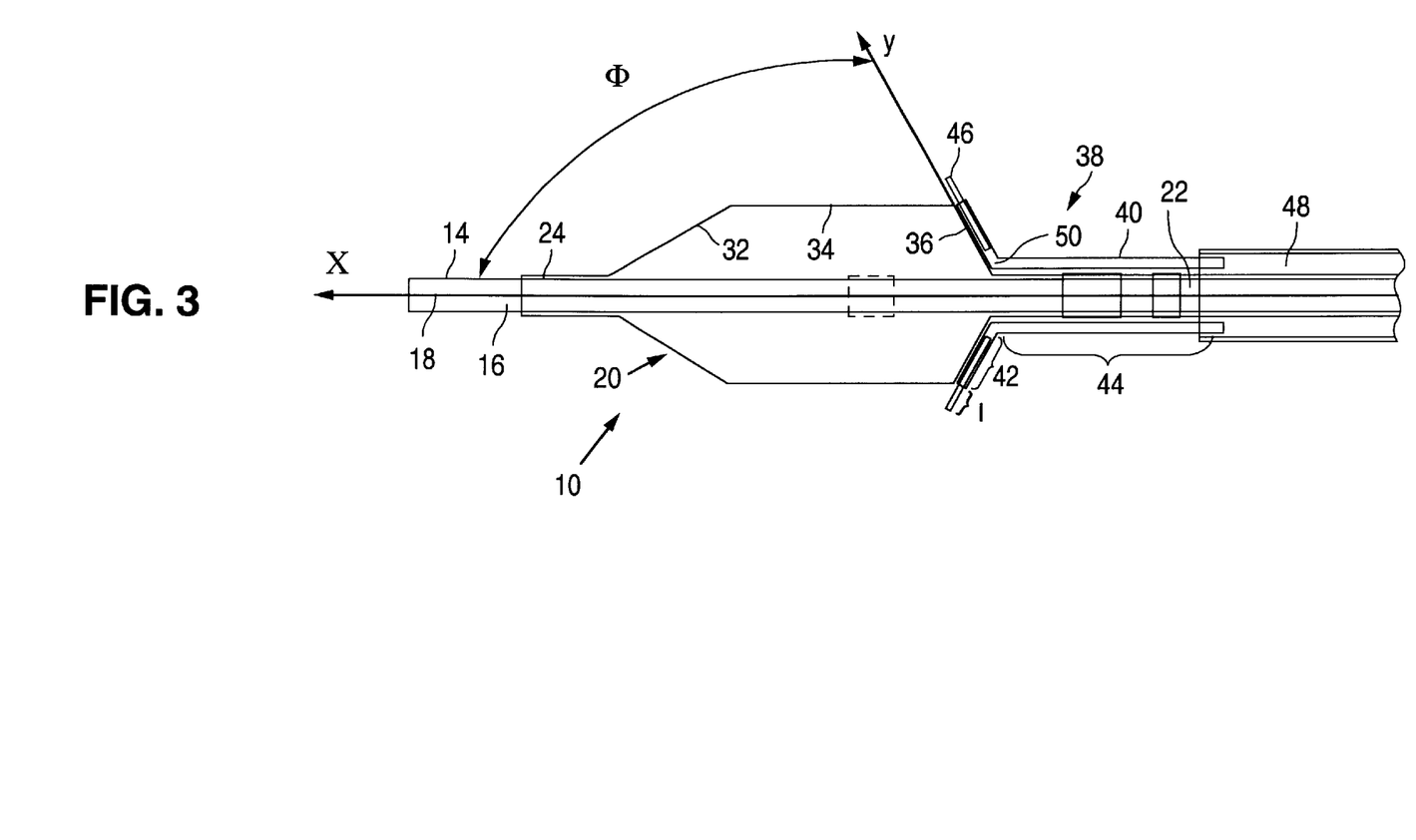
FIG. 3 is a partial cross-sectional view of another embodiment of a substance delivery apparatus of the present invention in the form of a catheter assembly having a balloon in an expanded configuration and a syringe assembly pivotally rotated toga delivery position.

Balloon 20 has a pair of opposing ends 24 and 26 engaged to catheter tube 12 to define a balloon chamber 28. Balloon 20 is formed from a balloon wall or membrane 30 which is selectively inflatable to dilate from a collapsed configuration to a desired and controlled expanded configuration. Balloon 20 can be selectively inflated by supplying a fluid into inflation lumen 22 at a predetermined rate of pressure, for example 1–20 atm. Balloon wall 30 is selectively deflatable, after inflation, to return to the collapsed configuration or a deflated profile. Balloon wall 30 can be defined by three sections, a distal wall 32, a medial wall 34, and a proximal wall 36. In one embodiment, as illustrated in FIG. 2, proximal wall 36 of balloon 20 is generally perpendicular to a longitudinal axis x of balloon 20, i.e., $\Phi$ is equal to about 90°, when balloon 20 is in the expanded configuration. In an alternative embodiment, as illustrated in FIG. 3, proximal wall 36 can taper from opposing end 26 at any suitable angle $\Phi$, typically between about 45° to less than about 90°, when balloon 20 is in the expanded configuration.

The three wall sections 32, 34, and 36 can be bound together by seams or be made out of a single seamless material. Balloon 20 can be made from any suitable material, including, but not limited to, polymers and copolymers of polyolefins, polyamides, polyesters and the like. The specific material employed must be mutually compatible with the fluids employed in conjunction with balloon 20 and must be able to stand the pressures that are developed within balloon chamber 28. Balloon wall 30 can have any suitable thickness so long as the thickness does not compromise properties that are critical for achieving optimum performance. The properties include high burst strength, low compliance, good flexibility, high resistance to fatigue, the ability to fold, the ability to cross and recross a desired region of treatment or an occluded region in a lumen, and low susceptibility to defect caused by handling. By way of example, and not limitation, the thickness can be in the range of about 10 microns to about 30 microns, the diameter of balloon 20 in the expanded configuration can be in the range of about 2 mm to about 10 mm, and the length can be in the range of about 3 mm to about 40 mm, the specific specifications depending on the procedure for which balloon 20 is to be used and the anatomy and size of the target lumen in which balloon 20 is to be inserted.

In accordance with another embodiment of the invention, balloon wall 30 can be made from a porous membrane. In one embodiment, the pores (not illustrated) are disposed on medial wall 34 segment of balloon wall 30 or any selected area thereof, while distal 32 and proximal 36 wall segments are impermeable. In another embodiment, pores can also be located on distal wall 32 and/or proximal wall 36 segments of balloon wall 30. The pores can have a wide range in size, for example from about 10 Å to less than about 5 $\mu$in diameter. The pore density can be in any suitable range, typically in the range of about $10^2$ to about $10^6$ pores per $cm^3$.

To inflate the porous membrane, a fluid, usefully a therapeutic substance solution, is supplied into inflation lumen 22 at a predetermined pressure, for example about 4 atm. During inflation, the pressure should not exceed about 20 atm so as to prevent significant leakage of the fluid from the pores. The specific pressure depends on factors such as the size of the pores, the thickness of balloon wall 30, the material from which balloon wall 30 is made, the type of substance employed, and the flow rate that is desired. A significant amount of leakage of the fluid during inflation is a drawback because the therapeutic substance will get carried off in the patient's blood stream which results in an ineffective treatment of the diseased region and exposure of the substance to healthy tissues. Porous balloon 20 can be used to deliver a substance to the tissues at a desired flow rate.

The flow rate of a substance is determined in units of ml/min and is dependent upon flow parameters such as pore density, pore size, viscosity of the composition, and applied pressure. As a general rule, flow parameters can be interrelated in the following manner: the flow rate is proportional to the pore density if all other flow parameters are constant; the flow rate is proportional to the diameter of the pore raised by the power of four; the flow rate is inversely proportional to the viscosity of the composition used; and the flow rate is proportional to the applied pressure.

Pore size of about 10 Å to about 5 $\mu$reduces the velocity at which the fluid is capable of traveling through a given pore, as compared to balloons having larger pore sizes, to prevent "jetting effect" that have significantly hindered the effectiveness of balloons having the larger pore sizes. "Jetting effect" is the velocity of liquid through a pore of a selected size at which trauma to the tissues occurs. The flow rate of delivery can be increased without increasing the velocity of the fluid through the pores. The flow rate of a fluid can be increased by increasing the pore density, which will provide the desired effect and delivery rate without increasing the fluid velocity.

The delivery apparatus includes a syringe assembly 38 for injecting a therapeutic substance into a tissue of a biological passageway. Syringe assembly 38 includes a hollow barrel 40 having a distal section 42 and a proximal section 44. Barrel 40 can be made from any suitable material such as polymers and copolymers of polyamides, polyolefins, polyurethanes, and alike. A hollow needle 46, for penetrating into a tissue of a biological passageway, is in fluid communication with distal section 42 of barrel 40. The portion of needle 46 protruding from barrel 40 can be of any predetermined length l, the specific length l dependent upon the desired depth of calibrated penetration and the procedure for which syringe assembly 38 is to be used. Usefully, length l can be from about 250 microns to about 1 mm. Proximal section 44 of barrel 40 is in fluid communication with a delivery lumen 48. Distal section 42 of barrel 40 is capable of pivotally rotating about an elbow 50 with respect to proximal section 44. Distal section 42 of barrel 40 is in communication with proximal wall 36 of balloon 20, and accordingly, needle 46 is capable of pivoting about elbow 50 in response to the expansion and retraction of balloon 20. In the collapsed configuration of balloon 20, as illustrated in FIG. 1, needle 46 of syringe assembly 38 is in a rested position, or in another words a longitudinal axis y of needle 46 is generally parallel to longitudinal axis x of balloon 20. The dilation of balloon 20 pivots needle 46 of syringe assembly 38 towards a selected delivery position, causing needle 46 to penetrate into a lumen wall. The extent of the rotation of distal section 42 is dependent upon the degree $\Phi$ at which proximal wall 36 of balloon 20 tapers from end 26 when balloon 20 is in the expanded configuration. In one embodiment, proximal wall 36 tapers at about 90° from end 26, causing longitudinal axis y of needle 46, at the delivery position, to be generally perpendicular to longitudinal axis x of balloon 20 when balloon 20 is in the expanded configuration. In an alternative embodiment, as illustrated in FIG. 3, longitudinal axis y of needle 46, at the delivery position, can be at any suitable angle $\Phi$, typically between about 45° to less than 90°.

In one embodiment, the delivery apparatus can include any suitable number of pivotally activated syringe assemblies 38, disposed about the periphery of balloon 20 and in communication with proximal wall 36. Each of syringe assemblies 38 can communicate with a respective, designated delivery lumen 48, two of which are illustrated as lumens 48a and 48b in FIGS. 1 and 2. The designated delivery lumens, e.g., delivery lumens 48a and 48b, can be in fluid communication with one another and/or in fluid communication with a common source of supply of a therapeutic substance. Each of syringe assemblies 38 is, therefore, capable of injecting the same therapeutic substance or the same combination of therapeutic substances.

In an alternative embodiment, each of the designated delivery lumens, for example illustrative lumens 48a and 48b, are not in fluid communication with one another. The designated lumens 48a and 48b allow each of syringe assemblies 38 to be in fluid communication with a different source of supply of a therapeutic substance. Accordingly, each of syringe assemblies 38 will be capable of delivering a different therapeutic substance or different combinations of substances.

Figure 4A:
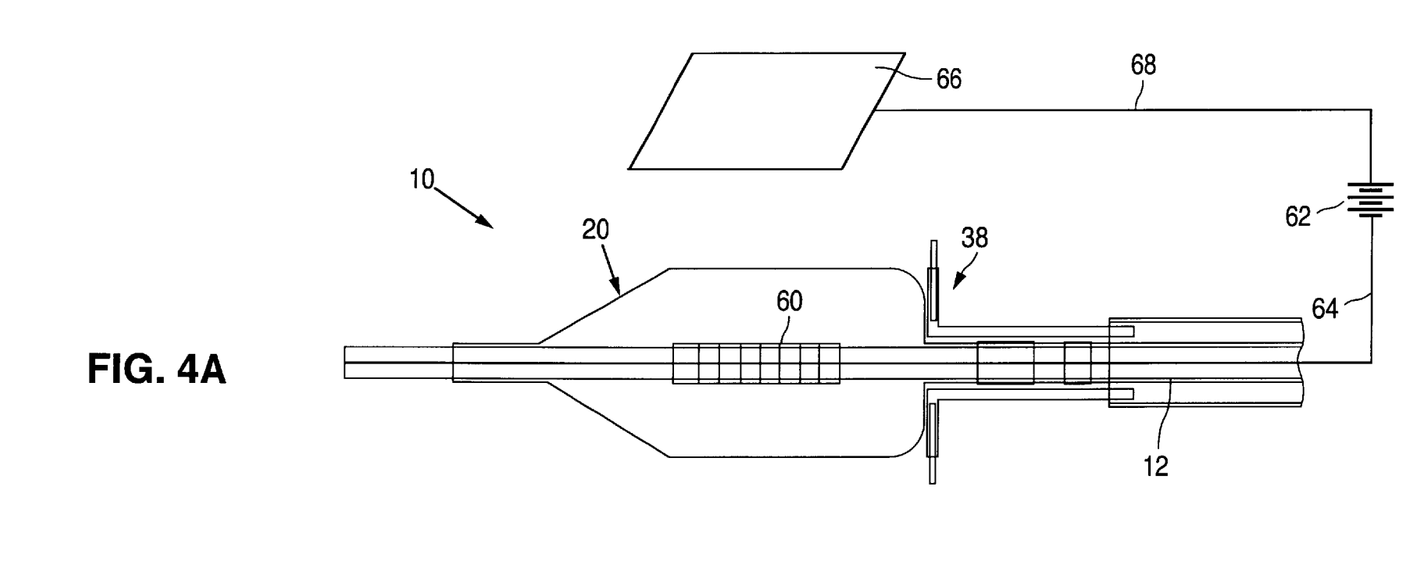
FIG. 4(a) is a partial cross-sectional view of another embodiment of a substance delivery apparatus of the present invention in the form of a catheter assembly having a balloon in an expanded configuration and a syringe assembly pivotally rotated to a delivery position, the delivery apparatus includes an iontophoreses element for providing a transport force for the substance.

In one embodiment, as illustrated by FIG. 4(a), iontophoresis technology, as is understood by one of ordinary skill in the art, can be used to drive ionic agents or drag nonionic agents that are in an ionic solution. In order for iontophoresis techniques to be utilized, the substance to be delivered should have an ionic nature or be bound to other ionic molecules. Iontopboresis can facilitate both transport of a substance across the porous membrane of balloon 20 and enhance tissue penetration of the substance. Referring to FIG. 4(a), a first electrode or first transport element 60 can be located within balloon 20 and is connected to a power supply 62 by a first lead 64. A second electrode or second transport element 66 can be located either on the surface of or within the subject's body and is connected to power supply 62 by a second lead 68 The power supply provides an electric signal between first and second electrodes 60 and 66. The signal can be direct or have a particular wave form. Examples of possible wave forms include a rectangular wave having a frequency of about 10 Hz or greater. Additionally, a series of waves can be intermittently passed between first and second electrodes 60 and 66 during the process of delivering the substance.

In another embodiment, ultrasonic or high frequency sound waves can be used to transport a substance through the porous membrane and into the surrounding tissue. Phonophoresis or sonophoresis has several advantages over iontophoresis, including the ability to achieve greater penetration into internal tissues of the vessel wall. Phonophoresis is also not limited to delivering only ionically charged forms of the substance.

Figure 4B:
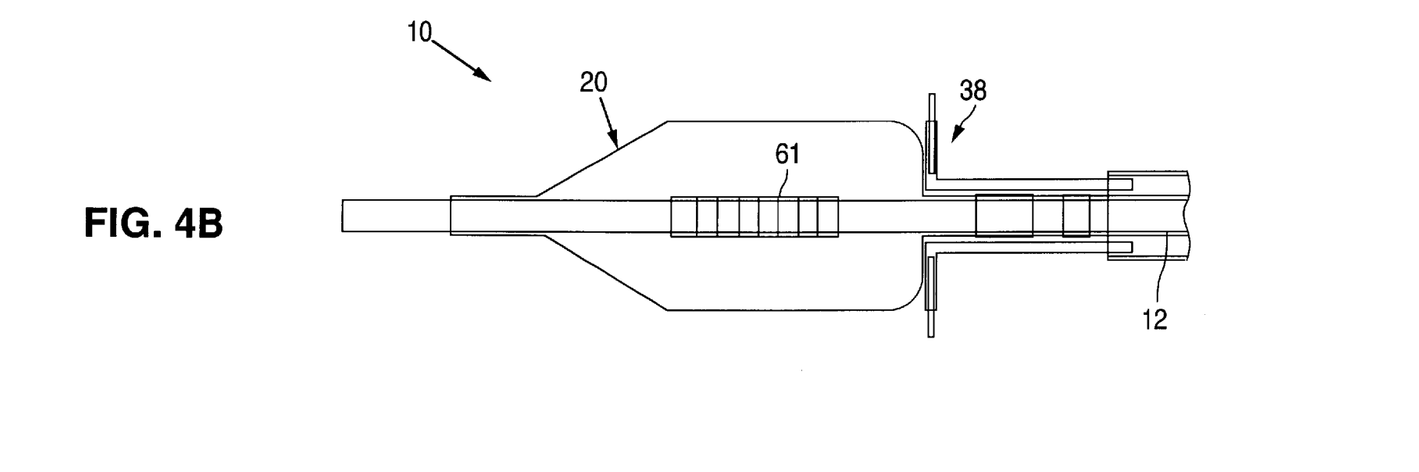
FIG. 4(b) is a partial cross-sectional view of another embodiment of a substance delivery apparatus of the present invention in the form of a catheter assembly having a balloon in an expanded configuration and a syringe assembly pivotally rotated to a delivery position, the delivery apparatus includes an ultrasonic transducer.

In addition to delivering a substance, ultrasound is advantageous because it can increase tissue temperature and capillary and cellular permeability. These results can enhance intra-tissue transport of a substance, enhance cellular uptake, and cause vasodilation/relaxation, which may be beneficial in vascular applications. Referring to FIG. 4(b), as is understood by one of ordinary skill in the art, an ultrasonic piezoelectric transducer 61 such as barium titanate, lead zirconale titanate, or the like, can be disposed within balloon 20 and is connected to a power supply through catheter tube 12. As a general rule, the diffusion rate of substances delivered by phonophoreses depends on the type of substances and the intensity and frequency of the ultrasonic field. Phonophoretic delivery techniques employ various frequencies of sonic waves, e g., about 1 MHz or less.

Method of Use

An application of the various embodiments of the present invention will be generally described by way of example with reference to the treatment of a blood vessel having an occlusion cause by restenosis. One of ordinary skill in the art should realize that the various embodiments of the present invention could be used in a variety of other medical applications.

Figure 5:
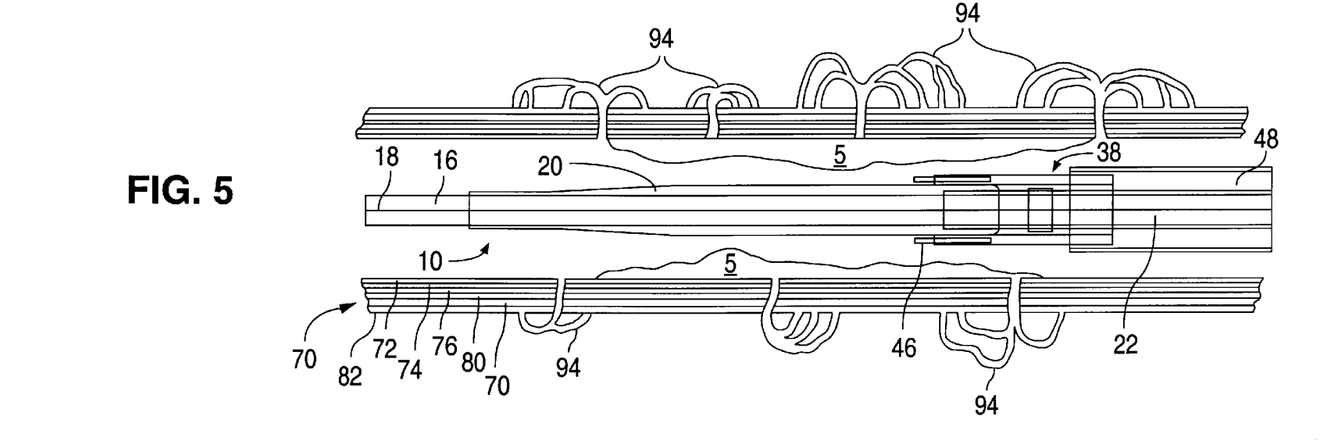
FIGS. 5 and 6 are illustrations of acts performed for delivering a therapeutic substance to the tissues of a blood vessel using one embodiment of the substance delivery apparatus of the present invention.
Figure 6:
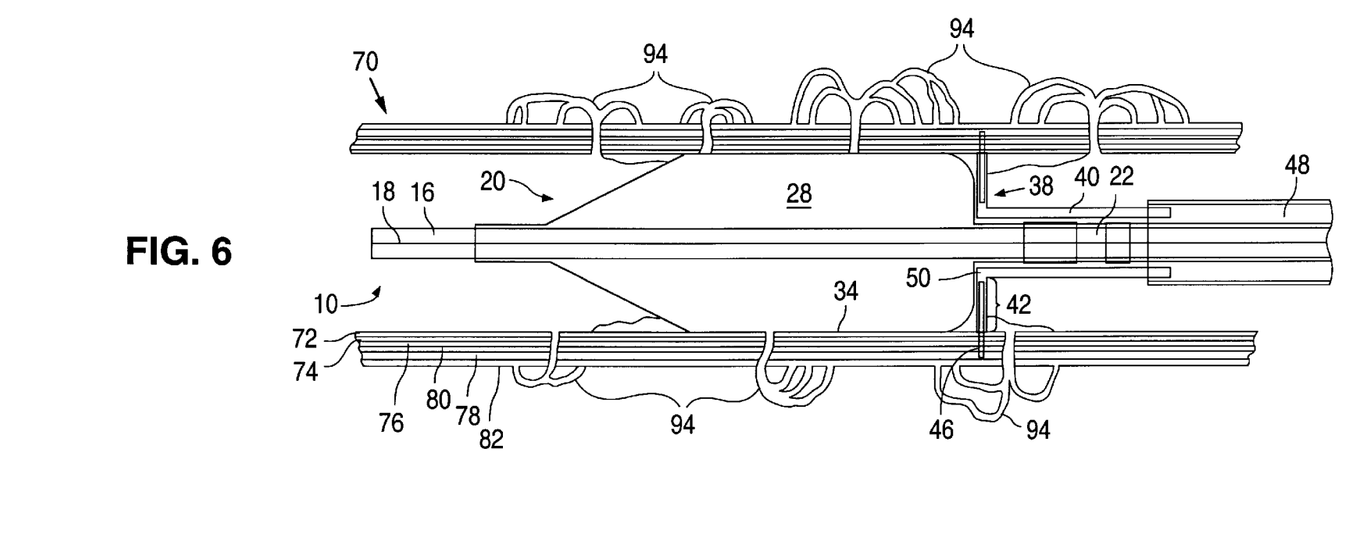

Referring to FIGS. 5 and 6, catheter assembly 10, having balloon 20 and syringe assembly 38, is advanced along guidewire 18 to a desired position in a vessel 70 so that balloon 20 overlays at least a portion of a stenotic lesion s. Balloon 20 can have either a porous or a nonporous membrane 30. Balloon 20 is inflated by introducing an inflation fluid into chamber 28 via inflation lumen 22. With a porous balloon 20, the inflation fluid can be a therapeutic substance or a combination of therapeutic substances. When balloon 20 is dilating to the expanded configuration, distal section 42 of syringe assembly 38 rotatably pivots outwardly about elbow 50, causing needle 46 to penetrate into the tissues of vessel 70 at a calibrated depth.

Figure 7:
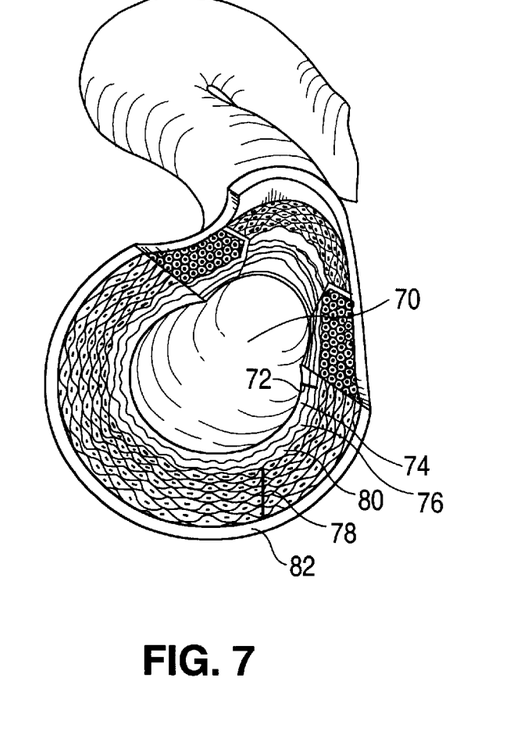
FIG. 7 is a cross-sectional view of a mammalian artery, illustrating each layer of the wall.

FIG. 7 illustrates a cross section of a wall of blood vessel 70. The walls are composed of three tunics: tunica intima 72 composed of squamous epithelium called endothelium 74 underlain by a subendothelial layer 76 of loose connective tissues; tunica media 78, separated from the tunica intima 72 by an internal elastic lamina 80, is made from smooth muscle cells (SMC) and elastic fibers; and tunica adventitia 82, the outer most layer, consists chiefly of connective tissues with irregularly arranged elastic and collagenous fibers. Proliferation and migration of SMC from the tunica media 78 to the tunica intima 74 causes an excessive production of extra cellular matrices (ECM), which is believed to be one of the leading contributors to the development of restenosis. Usefully, needle 46 should be calibrated so that it is capable of penetrating into the tunica media 78 layer to inhibit proliferation and migration of SMC and the development of ECM.

A therapeutic substance or a combination of therapeutic substances can be administered to the adventitia layer 82 and/or the media layer 78 via needle 46 by introducing the substance(s) through delivery lumen 48 at a selected pressure. Virtually any type of useful therapeutic substance of any given molecular size and weight can be injected through needle 46. Therapeutic substances having a molecular weight of less that about 5000 daltons are capable of penetrating through the intima layer 72. Thus, balloon 20 having porous membrane 30 can be used to administer such substances to the outer layers of the vessel wall. Therapeutic substances that are incapable of penetrating through intima layer 72 can be supplied by porous balloon 20 to the adventitia layer 82 via the vasa vasorum.

Figure 8:
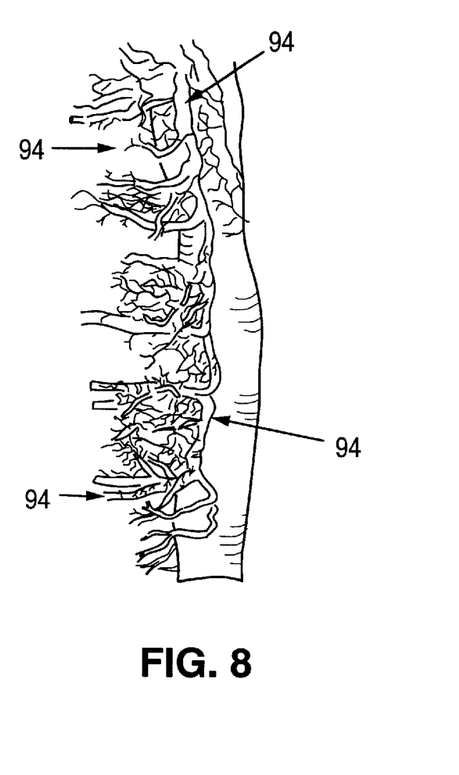
FIG. 8 is a partial prospective view of a mammalian vessel, illustrating the vasa vasorum networked along the tunica adventitia layer of the vessel.

Discharging of a therapeutic substance out from balloon 20 in an expanded configuration, having medial wall 34 compressed against the inner wall of blood vessel 70, causes the therapeutic substance to penetrate into the vasa vasorum of blood vessel 70. As best illustrated in FIG. 8, the tunica adventitia layer 82 is infiltrated with a network of tiny blood vessels, shown by arrows 94, called vasa vasorum. These "vessels of the vessels" nourish the more external tissue of the blood vessels (the inner portion obtains its nutrients directly from blood in the lumen). Discharge of a therapeutic substance into the vasa vasorum 94 causes such substances to be supplied to the tunica adventitia layer 82 of blood vessels.

Therapeutic substances or agents can include, but are not limited to, antineoplastic, antiinflammatory, antiplatelet, anticoagulant, antifibrin, antithrombin, antimitotic, antiproliferative, antibiotic, antioxidant, antiallergic substances, and combinations thereof. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analogue from Ibsen), angiotensin converting enzyme inhibitors such as Captopril® (available from Squibb), Cilazapril® (available from Hofman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. An example of an antiallergic agent includes Permirolast potassium. Other therapeutic substances or agents which may be appropriate include alpha-interferon, genetically engineered epithelial cells, dexamethasone, and growth factors such as FGF, PDGF, and VEGF. While the foregoing therapeutic substances or agents are well known for their preventative and treatment properties, the substances or agents are provided by way of example and are not meant to be limiting. Other therapeutic substances which are currently available or that may be developed are equally applicable for use with the present invention. The treatment of patients using the above-mentioned medicines is well known to those of ordinary skill in the art.

The catheter which includes syringe assembly 38 may be the same balloon catheter employed to dilate the vessel, thus combining the duel function of therapeutic substance delivery and dilation of the lesion into one catheter. Alternatively, a vessel may be dilated first with a catheter designed specifically for dilation, followed by insertion of a catheter having syringe assembly 38 for therapeutic substance delivery.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A substance delivery apparatus, comprising:
   (a) a catheter assemnbly;
   (b) a balloon disposed at an end portion of said catheter assembly, said balloon being configured to have a collapsed form and an expanded form;
   (c) a needle capable of penetrating into tissues of a subject for administering a substance to said subject; and
   (d) a hollow body in fluid communication with said needle, said hollow body being defined by a first section and a second section, wherein said first section is capable of pivotally rotating with respect to said second section in response to inflation of said balloon from said collapsed from to said expanded form, and wherein a longitudinal axis of said needle is generally parallel to a longitudinal axis of said balloon when said balloon is in said collapsed form.

2. The substance delivery apparatus of claim 1, wherein said balloon is made from a porous membrane.

3. The substance delivery apparatus of claim 1, additionally comprising a transport element operably integrated with said catheter assembly, said transport element having a first electrode element, a second electrode element, and a power supply electrically communicating with said first and second electrode elements, wherein said first electrode element is positioned within said balloon.

4. The substance delivery apparatus of claim 1, additionally comprising a transport element operably integrated with said catheter assembly, said transport element having an ultrasonic transducer.

5. The substance delivery apparatus of claim 1, wherein said longitudinal axis of said needle is about 45° to about 90° from said longitudinal axis of said balloon when said balloon is in an expanded form.

6. A therapeutic substance delivery apparatus, comprising:
   (a) a catheter assembly for insertion in a bodily lumen;
   (b) a balloon integrated with said catheter assembly, wherein said balloon is capable of being inflated to selectively dilate from a collapsed configuration to an expanded configuration and said balloon is capable of being deflated after inflation to retract to a deflated profile; and
   (c) a needle for delivering a therapeutic substance integrated with said catheter assembly, wherein said needle is essentially parallel to the longitudinal axis of the end portion of said catheter assembly when said balloon is in said collapsed configuration and said needle is positioned at an angle with respect to the longitudinal axis of the end portion of said catheter assembly when said balloon is in an expanded configuration.

7. The apparatus of claim 6, wherein said needle is calibrated to penetrate into the tunica media layer of a blood vessel for administering said therapeutic substance to a region of the tunica media layer of said blood vessel.

8. The apparatus of claim 6, wherein said balloon is made from a membrane having a plurality of pores for allowing a therapeutic substance supplied into said balloon to be discharge out from said pores.

9. The apparatus of claim 6, wherein said angle is about 45° to about 90° from the longitudinal axis of the end portion of said catheter assembly.

* * * * *

UNITED STATES PATENT AND TRADEMARK OFFICE
CERTIFICATE OF CORRECTION

PATENT NO. : 6,494,862 B1
DATED : December 17, 2002
INVENTOR(S) : Ray et al.

It is certified that error appears in the above-identified patent and that said Letters Patent is hereby corrected as shown below:

Column 9,
Line 16, change "assemnbly" to -- assembly --.
Line 28, change "from" to -- form --.

Signed and Sealed this

Eighteenth Day of March, 2003

JAMES E. ROGAN
*Director of the United States Patent and Trademark Office*